(12) United States Patent
Eibschitz-Tsimhoni

(10) Patent No.: US 6,629,980 B1
(45) Date of Patent: Oct. 7, 2003

(54) INSTRUMENT AND METHOD FOR CREATING AN INTRAOCULAR INCISION

(75) Inventor: Maya Eibschitz-Tsimhoni, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 378 days.

(21) Appl. No.: 09/724,252

(22) Filed: Nov. 28, 2000

(51) Int. Cl.[7] .............................................. A61B 17/32
(52) U.S. Cl. ....................... 606/107; 606/166; 606/170
(58) Field of Search ................................ 606/107, 166, 606/167, 170, 171, 180, 181; 604/22, 289, 294; 30/400, 29, 49, 113.1, 174, 165

(56) References Cited

U.S. PATENT DOCUMENTS

| | | | |
|---|---|---|---|
| 783,010 A | * | 2/1905 | Beckham .................... 30/113.1 |
| 979,505 A | * | 12/1910 | Johnson ........................ 606/181 |
| 1,374,289 A | * | 4/1921 | Dunkley ..................... 30/113.1 |
| 1,994,366 A | * | 3/1935 | Mellor ........................ 30/113.1 |
| 2,583,577 A | * | 1/1952 | Kingsbury ................. 30/279.2 |
| 4,676,243 A | | 6/1987 | Clayman |
| 4,706,669 A | * | 11/1987 | Schlegel ...................... 606/107 |
| 4,766,897 A | | 8/1988 | Smirmaul |
| 4,869,716 A | * | 9/1989 | Smirmaul .................... 604/22 |
| 4,911,161 A | | 3/1990 | Schechter |
| 4,950,272 A | * | 8/1990 | Smirmaul ................... 606/107 |
| 5,122,152 A | * | 6/1992 | Mull ........................... 606/170 |
| 5,135,530 A | | 8/1992 | Lehmer |
| 5,203,865 A | * | 4/1993 | Siepser ....................... 606/166 |
| 5,261,923 A | | 11/1993 | Soares |
| 5,269,787 A | | 12/1993 | Cozean, Jr. et al. |
| 5,397,333 A | * | 3/1995 | Knoepfler ................... 606/170 |
| 5,423,841 A | | 6/1995 | Kornefeld |
| 5,451,230 A | * | 9/1995 | Steinert ...................... 606/107 |
| 5,591,183 A | * | 1/1997 | Chin ........................... 606/159 |
| 5,669,922 A | * | 9/1997 | Hood .......................... 606/169 |
| 5,728,117 A | | 3/1998 | Lash |
| 5,776,154 A | * | 7/1998 | Taylor et al. ................ 606/167 |
| 5,860,994 A | | 1/1999 | Yaacobi |
| 5,873,883 A | | 2/1999 | Cozean, Jr. et al. |
| 5,893,862 A | * | 4/1999 | Pratt et al. .................. 606/170 |
| 6,152,894 A | * | 11/2000 | Kubler ........................ 604/22 |
| 6,165,190 A | * | 12/2000 | Nguyen ...................... 606/166 |
| 6,447,528 B2 | * | 9/2002 | Paraschac ................... 606/190 |
| 2002/0055753 A1 | * | 5/2002 | Silvestrini ................... 606/166 |

OTHER PUBLICATIONS

Howard V. Gimbel, M.D., "Cases, Instruments and Notes," J. Cataract Refract Surg—vol. 16, Mar. 1990, pp. 246–249.

Howard V. Gimbel, M.D. et al., "Development, Advantages, and Methods of the Continuous. Circular Capsulorhexis Technique," J. Cataract Refract Surg—Vo. 16, Jan. 1990, pp. 31–37.

Steve Arshinoff, M.D., "Mechanics of Capsulorhexis," J. Cataract Refract Surg—vol. 18, Nov. 1992, pp. 623–628.

(List continued on next page.)

Primary Examiner—A. Vanatta
(74) Attorney, Agent, or Firm—Brooks & Kushman P.C.

(57) ABSTRACT

An instrument and method are provided for incising an intraocular tissue, such as the anterior capsule of the eye, which requires only a small wound cut in the corneal or scleral tissue. The instrument includes a handle and a curvilinear head portion attached to the handle. The head portion includes spaced first and second ends which define an opening therebetween, wherein the head portion is preferably generally semicircular in form. The head portion further includes a first cutting edge which is operable to engage the intraocular tissue and penetrate at least partially through the intraocular tissue to create a first curvilinear incision therein. Creating a second curvilinear incision in the intraocular tissue adjacent the first incision results in a continuous curvilinear, preferably generally circular, tissue flap incised in the intraocular tissue.

22 Claims, 4 Drawing Sheets

OTHER PUBLICATIONS

Daniel Wasserman, MD et al., "Anterior Capusular Tears and Loop Fixation of Posterior Chamber Intraocular Lenses," Opththamology, 1991, pp. 425–431.

A. Panda et al., "Neodymium: Yttrium Aluminum Garnet Laser Anterior Capsulotomy," Annuals of Ophthalmology, Sep. 1991, Vo. 23, No. 9, pp. 334–336.

Norbert Hausmann et al., "Investigations on Diathermy for Anterior Capsulotomy," Investigative Ophthalmology & Visual Science, vol. 32, No. 7, Jun. 1991, pp. 2155–2159.

Rasik B. Vajpayee et al., "Capsulotomy for Phacoemulsification in Hypermature Cataracts," J. Cataract Refract Surg—vol. 21, Nov. 1995, pp. 612–615.

Oliver D. Schein, MD et al., "Cataract Surgical Techniques," Arch Ophthalmol/vol. 113, Sep. 1995, pp. 1108–1112.

C. I. Phillips, "Erisocapsulorhexis," J. Cataract Refract Surg—vol. 17, Jan. 1991, pp. 111.

Okihiro Nishi, M.D., "Intercapsular Cataract Surgery with Lens Epithelial Cell Removal Part I: Without Capsulorhexis," J. Cataract Refract Surg—vol. 15, May 1989, pp. 297–300.

Okihiro Nishi, M.D. et al., "Endocapsular Phacoemulsification Following Buttonhole Anterior Capsulotomy: A Preliminary Report", J. Cataract Refract Surg. vol. 16, Nov. 1990, pp. 757–762.

Okihiro Nishi, M.D., "Micropunch for Buttonhole Anterior Capsulotomy in Endointercapsular Cataract Surgery," Arch Ophthalmol—vol. 108, Jun. 1990, pp. 892–893.

Robert M. Feibel, M.D., "Modification of the Bent Needle Technique for Anterior Capsulotomy," Ophthalmic Surgery, Dec. 1986, vol. 17, No. 12, pp. 819–820.

Frederick A. Richburg M.D., "Neodymium: YAG Laser for Anterior Capsulotomy,"AM Intraocular Implant Soc J—vol. 11, Jul. 1985, pp. 372–375.

Richard M. Comer et al., "Radiofrequency Diathermy Capsulorhexis of the Anterior and Posterior Capsules in Pediatric Cataract Surgery: Preliminary Results," J. Cataract Refract Surf—vol. 23, Supplement 1, 1997, pp. 641–644.

David T. Ng et al., "Intraoperative Complications of 1000 Phacoemulsification Procedures: A Prospective Study," J. Cataract Refract Surg—vol. 24, Oct., 1998, pp. 1390–1395.

Stephen A. Obstbaum M.D., "The Anterior Capsulotomy Revisited," J. Cataract Refract Surg—vol. 24, Feb., 1998, pp. 143–144.

Kenneth J. Hoffer et al., "Intracameral Subcapsular Fluorescein Staining for Improved Visualization During Capsulorhexis in Mature Cataracts," J. Cataract Refract Sug—vol. 19, Jul. 1993, pp. 566.

* cited by examiner

INSTRUMENT AND METHOD FOR CREATING AN INTRAOCULAR INCISION

TECHNICAL FIELD

This invention relates to an instrument and method for creating an incision in an intraocular tissue, such as the anterior capsule of the eye.

BACKGROUND ART

An individual's vision involves the eye forming an image of an object and sending that image to the sensory centers of the brain. An object will reflect light through the cornea, the aqueous humor, the pupil, the lens, and the vitreous humor of the eye, wherein the reflective light is focused by the lens onto the retina (see FIG. 1). The nerve fibers within the retina collectively leave the eye in the optic nerve and enter the brain where the visual signals are processed.

Among other factors, therefore, the quality of vision depends upon the transparency of the lens. An opacity of the lens, commonly known as cataract, may prevent a clear image from forming on the retina. The lens is encapsulated by a cellophane-like membrane covering its anterior and posterior surfaces, wherein the capsule is retained in position chiefly by suspensory ligaments termed zonules. Cataracts may be age-related, congenital or result from trauma, disease or medications, and are generally treated by performing extracapsular cataract extraction. In this procedure, an opening is provided in the anterior lens capsule through which instrumentation can enter and the opaque lens is removed and replaced by an artificial intraocular lens.

Each year, approximately 1.3 million cataract surgeries are performed in the United States, and several methods have been utilized for opening the anterior lens capsule to gain access to the lens nucleus and cortical material. Currently, the two most popular techniques for anterior capsulotomy are the "can-opener" technique and capsulorrhexis. In can-opener capsulotomy, a cystotome, knife, or needle is inserted through a small incision in the sclera or peripheral cornea and small connecting tears are made in the anterior lens capsule in a circular pattern. When a complete circle has been made by connecting the tears, a circular piece of the anterior capsule is then grasped with forceps and torn away along the perforations. Unfortunately, when opening the capsule with numerous small capsular tears, the small tags which remain become a focal area of least resistance and can lead to tears which extend radially and posteriorly to the posterior capsule. The detrimental result is a loss of structural stability of the capsule and an increased likelihood of vitreous entry into the anterior chamber.

Capsulorrhexis denotes a circular central opening in the anterior capsule. This continuous opening eliminates the residual tags common with the can-opener technique described above. In capsulorrhexis, a capsular incision is made with a cystotome, and this incision is coaxed to form a circular shape by pushing the leading edge of the freshly tearing capsule with the cystotome in a non-cutting fashion or by grasping the leading edge with forceps. This procedure is quite difficult to control by the surgeon. The tearing motion can lead to an undesirable tear toward the equator and the posterior capsule, and the opening size is hard to control. As such, capsulorrhexis requires a significant amount of skill, experience, and learning time to consistently obtain successful results.

As described above, opening the anterior capsule via an anterior capsulotomy is a very delicate procedure and is widely considered to be one of the most difficult steps in a cataract surgery. A poorly performed anterior capsulotomy significantly increases the difficulty in performing the subsequent surgical steps and the probability of operative complications. Complications resulting from a poor capsulotomy include zonular stress with subsequent breakage of the posterior capsule, vitreous loss, and large capsular tags preventing efficient lens removal. A poor capsulotomy also prevents placement of an intraocular lens in the capsular bag due to ill-defined capsular structures. Such complications are unfortunately frequent. An unsuccessful capsulotomy increases the risk of intraoperative complications such as vitreous loss and inability to implant a posterior chamber intraocular lens. The operative time and patient discomfort are increased, along with the risk of postoperative complications with decreased final best-corrected visual acuity results.

Furthermore, with either of the above-described techniques for anterior capsulotomy, the capsular opening's size or position is often not ideal. The location, size, and configuration of the incision have important consequences. For example, a small capsular opening can impair the safe removal of the lens nucleus and cortex and prevent proper intraocular lens insertion into the lens capsule. In addition, the excessive stress placed on the lens capsule which result from having to work with a small or eccentric capsular opening puts the eye at risk for zonular and capsular breakage.

Certain devices have been proposed to overcome the problems associated with conventional anterior capsulotomy techniques. For example, U.S. Pat. No. 4,766,897 issued to Smirmaul, and U.S. Pat. Nos. 5,269,787 and 5,873,883 issued to Cozean Jr. et al. each disclose instruments which include circular cutting members for incising the anterior capsule. However, use of such devices in small incision cataract surgery is limited due to their size. More particularly, the anterior lens capsule of the eye is shielded by the cornea and sclera, such that a passage wound must be cut in the corneal or scleral tissue before any surgical apparatus can reach the anterior capsule. It is desirable to have the width of the passage wound cut on the tissue as small as possible, preferably on the order of 2.4 to 2.7 mm in width. A small wound decreases the necessary surgical closing procedures, promote rapid healing, minimizes astigmatism, reduces potential infections, and offers rapid visual rehabilitation. Therefore, the instrumentation employed in cataract surgery should be capable of passing through a small wound.

In an attempt to meet this size requirement, alternative surgical devices have been proposed. For example, U.S. Pat. No. 5,135,530 issued to Lehmer discloses a deformable circular cutting ring which is provided between the two forward positions of two elongated arms. The arms crisscross each other and are hinged together, such that when the rearward portions of the two arms are squeezed toward each other, the forward positions of the two arms will move toward each other to compress the deformable circular cutting ring into a narrow elliptical shape. The overall width of the narrow elliptical shaped deformable circular cutting ring and the forward portions of the two elongated arms is small enough to be inserted into the anterior chamber of the eye through a small tissue wound of about 4 mm in width.

Similarly, U.S. Pat. No. 5,728,117 issued to Lash discloses a capsulorrhexis instrument that includes a flexible band having a cutting edge. The band is fixed to a plunger, and is retractable within a tube and extendable into a position projecting out of the tube. While in its retracted position within the tube, the band assumes a narrow elliptical shape. However, when the flexible band is in its extended position outside of the tube, such as inside the eye, it deforms into a circular shape for incising intraocular tissue.

While these deformable devices provide one solution to the size constraint imposed by a small tissue wound, the devices suffer from the disadvantages of being overly complex as well as costly to manufacture and maintain. Therefore, a need exists for an improved instrument and method for creating an intraocular incision within the constraints of small incision cataract surgery.

DISCLOSURE OF INVENTION

Therefore, it is an object according to the present invention to provide an instrument and method for incising an intraocular tissue which is capable of creating an incision of suitable size for lens removal, yet which requires only a small entry wound cut on the corneal or scleral tissue.

It is another object according to the present invention to provide an instrument and method for incising an intraocular tissue which allows for precise control over the location and size of the resulting incision.

It is yet another object according to the present invention to provide an instrument and method for incising an intraocular tissue which is easy to operate and simple and cost-efficient to manufacture.

Accordingly, an instrument is provided for incising an intraocular tissue, such as the anterior capsule of the eye. The instrument includes a handle and a curvilinear head portion attached to the handle. The head portion includes spaced first and second ends which define an opening therebetween. The head portion further includes a cutting edge which is operable to engage the intraocular tissue and penetrate at least partially through the intraocular tissue to create a curvilinear incision therein.

In one embodiment, the head portion includes a second cutting edge opposing the first cutting edge. The head portion is preferably generally semicircular, and has a radius of about 2 to 3 mm, and a width of about 1 mm in order to accommodate a narrow corneoscleral wound. Furthermore, the head portion can be attached to the handle at an angle relative to a longitudinal axis of the handle. The handle and head portion are constructed from a plastic, metallic, or other suitable material.

In further accordance with the present invention, a surgical kit for incising an anterior capsule of an eye is provided. The kit includes a first instrument having a handle and a curvilinear head portion attached to the handle, where the first instrument head portion includes spaced first and second ends which define an opening therebetween having a first orientation. First instrument head portion further includes a cutting edge which is operable to engage the anterior capsule and penetrate at least partially therethrough to create a first curvilinear incision therein. The kit further includes a second instrument having a handle and a curvilinear head portion attached to the handle, where the second instrument head portion includes spaced first and second ends which define an opening therebetween having a second orientation which opposes the first orientation. Second instrument head portion further includes a cutting edge which is operable to engage the anterior capsule and penetrate at least partially therethrough to create a second curvilinear incision therein. Creating adjacent first and second incisions results in a continuous curvilinear tissue flap incised in the anterior capsule.

Correspondingly, a method is provided for incising an intraocular tissue. The method includes creating a wound in one of a corneal region and a scleral region of the eye. Next, the method includes inserting an instrument through the wound and into proximity with the intraocular tissue, where the instrument includes a handle and a curvilinear head portion attached to the handle, and the head portion includes a cutting edge. The method further includes engaging the intraocular tissue with the cutting edge and penetrating at least partially through the intraocular tissue in order to create a curvilinear incision therein.

In greater particularity, a method is provided for incising an anterior capsule of an eye which includes creating a wound in one of a corneal region and a scleral region of the eye, and inserting a first instrument through the wound and into proximity with the anterior capsule. The first instrument includes a handle and a generally semicircular head portion attached to the handle. The first instrument head portion includes a first cutting edge having a first orientation. Next, the method includes engaging the anterior capsule with the first cutting edge and penetrating at least partially through the anterior capsule in order to create a first generally semicircular incision therein. The method further includes inserting a second instrument through the wound and into proximity with the anterior capsule. The second instrument includes a handle and a generally semicircular head portion attached to the handle. The second instrument head portion includes a second cutting edge having a second orientation which opposes the first orientation. Still further, the method includes engaging the anterior capsule with the second cutting edge and penetrating at least partially through the anterior capsule in order to create a second generally semicircular incision therein adjacent the first incision, thereby resulting in a generally circular tissue flap incised in the anterior capsule.

In a preferred embodiment, the wound created in the corneal or scleral tissue is less than about 4 mm in length. In addition, the method preferably further includes removing the first instrument through the wound prior to inserting the second instrument. Furthermore, the method can also include injecting a viscoelastic fluid into an anterior chamber of the eye, and monitoring the first and second instruments with a microscope. Still further, the method can include applying a dye to the first cutting edge, the dye being deposited on the anterior capsule in response to engagement of the first cutting edge with the anterior capsule.

An alternative method for incising an anterior capsule of an eye according to the present invention includes creating a wound in one of a corneal or scleral region of the eye, and inserting an instrument through the wound and into proximity with the anterior capsule. The instrument includes a handle and a generally semicircular head portion attached to the handle, where the head portion has first and second opposed cutting edges. The method further includes engaging the anterior capsule with the first cutting edge and penetrating at least partially through the anterior capsule in order to create a first generally semicircular incision therein. Next, the method includes rotating the instrument approximately 180° about a longitudinal axis of the handle. Still further, the method includes engaging the anterior capsule with the second cutting edge and penetrating at least partially through the anterior capsule in order to create a second generally semicircular incision therein adjacent the first incision, thereby resulting in a generally circular tissue flap incised in the anterior capsule.

The above objects and other objects, features, and advantages of the present invention are readily apparent from the

BRIEF DESCRIPTION OF DRAWINGS

FIG. 3 is a top plan view of the instrument of FIG. 2a;

BEST MODE FOR CARRYING OUT THE INVENTION

Figure 1:
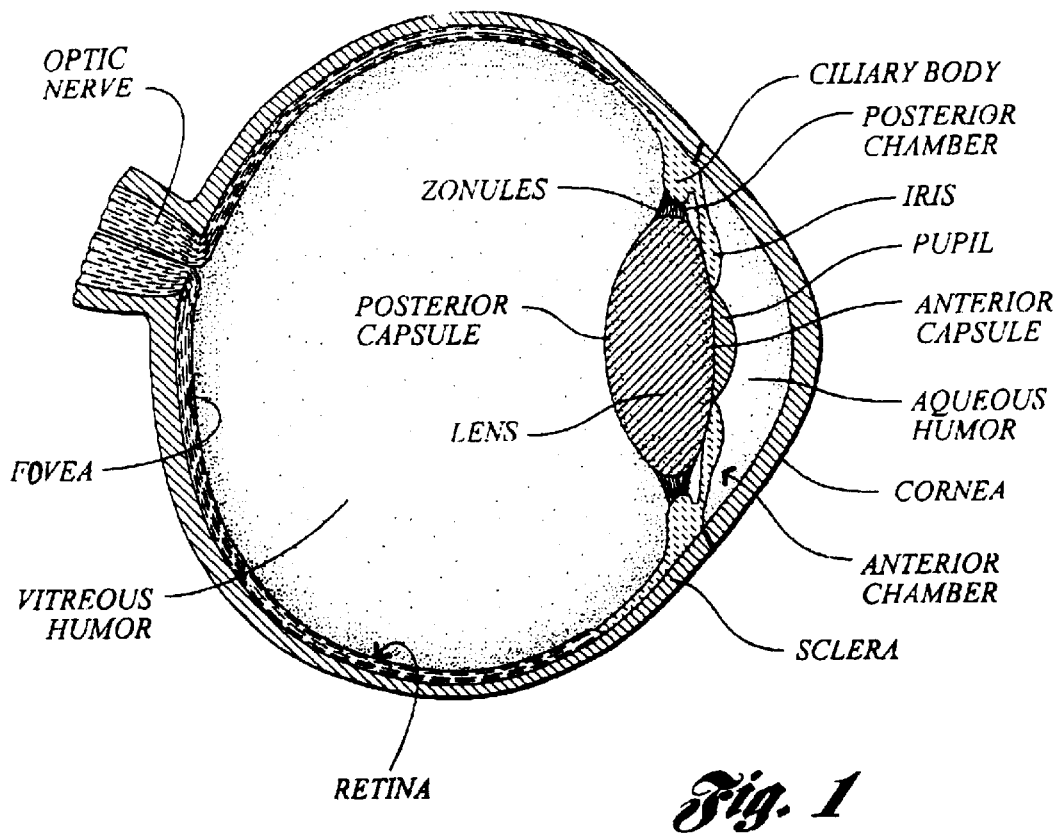
FIG. 1 is a cross-sectional view illustrating the human eye.
Figure 2A:
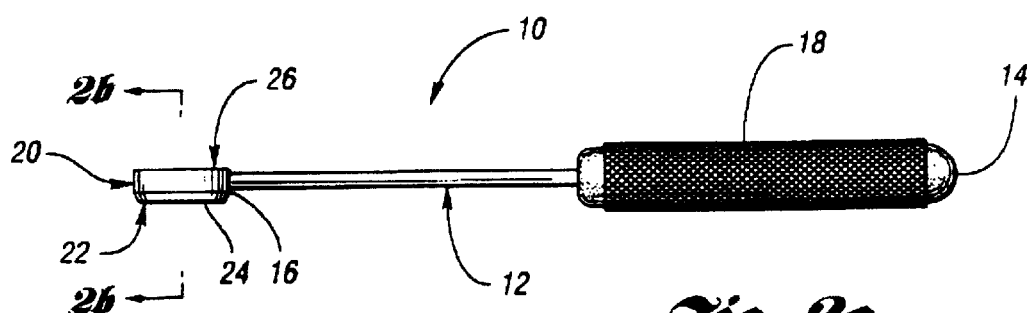
FIG. 2a is a side elevational view of an instrument for incising an intraocular tissue in accordance with the present invention, wherein one cutting edge is provided and the head portion has a right-facing orientation.
Figure 2B:
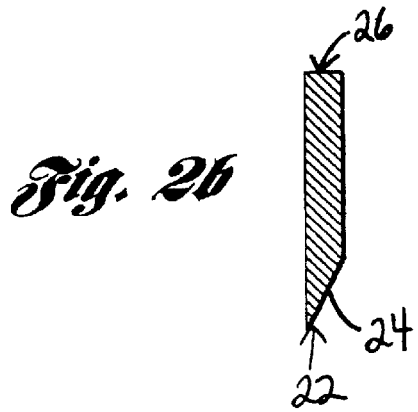
FIG. 2b is a cross-sectional view of the head portion of FIG. 2a taken along line 2b—2b.
Figure 3:
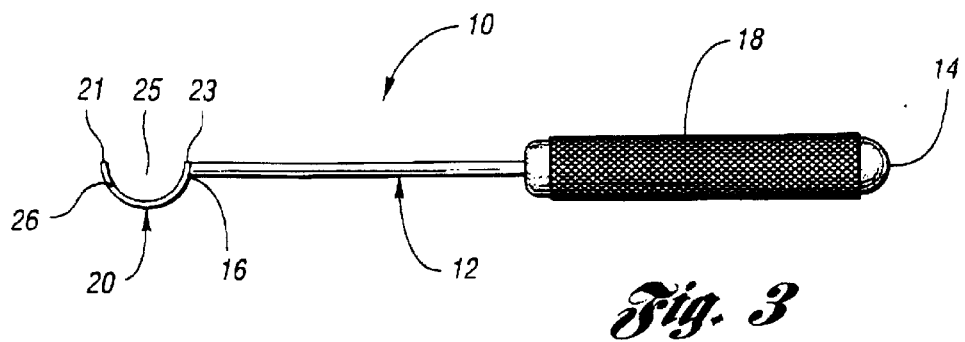

Referring first to FIGS. 2–3, an instrument, designated by reference numeral 10, for incising an intraocular tissue is shown constructed in accordance with the present invention. Instrument 10 is designed for use during an ophthalmic surgical procedure, such as in an anterior capsulotomy during cataract surgery, where an incision is required in an intraocular tissue. Instrument 10 is capable of being inserted through a small wound, which can be less than about 4 mm, cut in the corneal tissue or scleral tissue and into the anterior chamber of the eye (see FIG. 1 for eye anatomy). Instrument 10 then engages the intraocular tissue, namely the anterior lens capsule, in order to create an adequate sized incision in the anterior capsule so that the natural lens of the eye can be removed.

As shown in FIGS. 2–3, instrument 10 includes an elongated handle 12, which can be solid or hollow and preferably of circular cross-section. Handle 12 can be of any length appropriate for the intended surgical procedure. For use in an anterior capsulotomy procedure, handle 12 is typically about 5 cm in length. Handle 12 has a proximal end 14 and a distal end 16, and preferably includes an enlarged portion 18 for grasping purposes. Handle 12 can also include an exterior grip surface, such as a knurled surface, to provide the operator with sufficient grip and manipulation of the instrument 10 during use.

Referring again to FIGS. 2 and 3, instrument 10 further includes a curvilinear head portion 20 attached to or near the distal end 16 of handle 12. Head portion 20 includes spaced first 21 and second 23 ends which define an opening 25 therebetween. In a preferred embodiment, head portion 20 is generally semicircular in shape, and can be constructed to be solid or hollow. Head portion 20 may be integrally formed with handle 12 or affixed thereto by welding or the like. In order to accommodate a small corneal/scleral wound on the order of 4 mm or less in length, head portion 20 is constructed to have a radius of between about 0.5 to 4 mm, and most preferably about 2 to 3 mm. Likewise, the width of head portion 20 is designed to be less than 3 mm, and most preferably about 1 mm. Of course, instrument 10 can be manufactured in many different dimensions such that the surgeon can select an instrument which is customized to the needs of a particular patient. For example, children's eyes are smaller than those of adults, such that head portion 20 should be designed to have a reduced width and radius when intended for use in pediatric surgical procedures.

As best shown in FIG. 2b, head portion 20 includes a bottom surface 22 having a cutting edge 24, where cutting edge 24 is operable to engage the intraocular tissue and penetrate at least partially through the tissue to create a curvilinear, or preferably generally semicircular, incision therein. More particularly, instrument 10 depicted in FIGS. 2 and 3 will create a generally semicircular incision with a first, right-facing orientation. Head portion 20 includes a second surface 26 opposing the first surface 22 (FIGS. 2 and 3), wherein the second surface 26 is preferably smooth to avoid injury of intervening tissue while inserting and removing instrument 10 from the anterior chamber.

Figure 4:
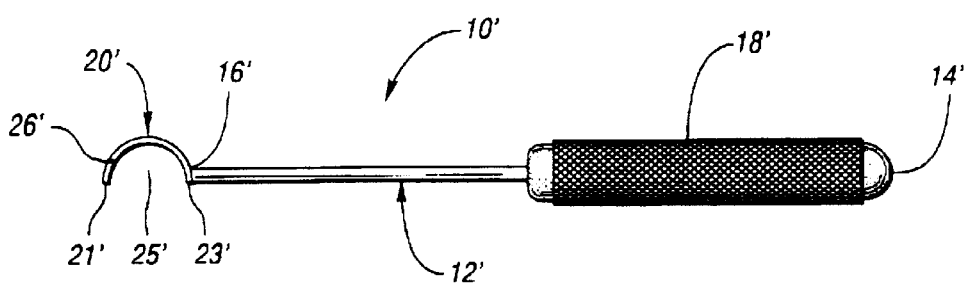
FIG. 4 is a top plan view of an instrument in accordance with the present invention wherein the head portion has a left-facing orientation.
Figure 10:
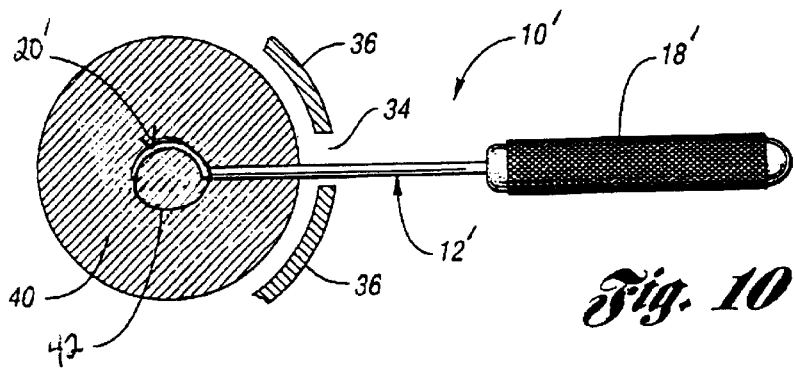
FIG. 10 is a top plan view illustrating the creation of a second generally semicircular incision in the anterior capsule adjacent the first incision using a left-facing instrument in accordance with the present invention.
Figure 11:
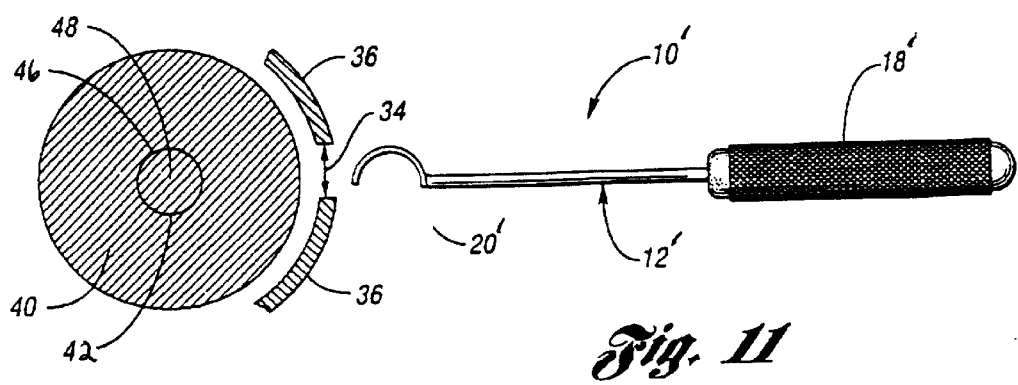
FIG. 11 is a top plan view illustrating removing the instrument of FIG. 10 through the wound, wherein a generally circular tissue flap in the anterior capsule has been formed by creating the first and second incisions.

In practice, a continuous curvilinear, preferably generally circular, incision is required in the anterior capsule in order to remove the natural lens material and also to insert an artificial intraocular lens. Therefore, as shown in FIG. 4, a second instrument 10' is provided in accordance with the present invention, wherein the reference numerals for instrument 10' correspond to those for instrument 10 except for the addition of a prime (') designation. Instrument 10' has a generally semicircular head portion 20' with a second, left-facing orientation, such that instruments 10 and 10' can be used successively to create the desired circular tissue flap. More particularly, instruments 10 and 10' could be included in a surgical kit for incising an intraocular tissue, such as the anterior capsule. As described below with reference to FIGS. 7–11, cutting edge 24 of instrument 10 is operable to engage the anterior capsule and penetrate at least partially therethrough to create a first generally semicircular incision therein (FIG. 9). Then, cutting edge 24' of instrument 10', having an orientation which opposes that of instrument 10, is operable to engage the anterior capsule and penetrate at least partially therethrough to create a second generally semicircular incision therein (FIG. 10). Creating adjacent first and second incisions using instruments 10 and 10' results in a continuous, generally circular tissue flap incised in the anterior capsule (FIG. 11).

Figure 5A:
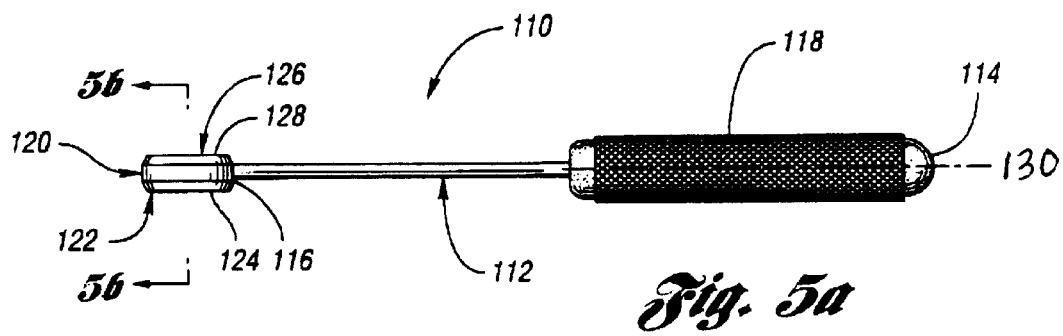
FIG. 5a is a perspective view of an alternative embodiment of the instrument of the present invention, wherein two cutting edges are provided.
Figure 5B:
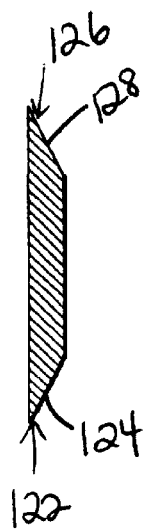
FIG. 5b is a cross-sectional view of the head portion of FIG. 5b taken along line 5b—5b.

Referring now to FIGS. 5a and 5b, an alternative instrument 110 can be provided, wherein reference numerals for instrument 110 correspond to those for instrument 10 except for the addition of a "1" prefix. Head portion 120 of instrument 110 has a second surface 126 which includes a cutting edge 128. Therefore, after cutting edge 124 can be used to make a first incision, instrument 110 is rotated approximately 180° about the handle longitudinal axis 130, and a second incision is made with cutting edge 128 adjacent the first incision in order to complete the circle. For any of instruments 10, 10', or 110, the cutting edges need only to structurally weaken the tissue along the engagement site, after which the anterior capsule can be coaxed to tear along the engagement site and the tissue flap removed.

Figure 6A:
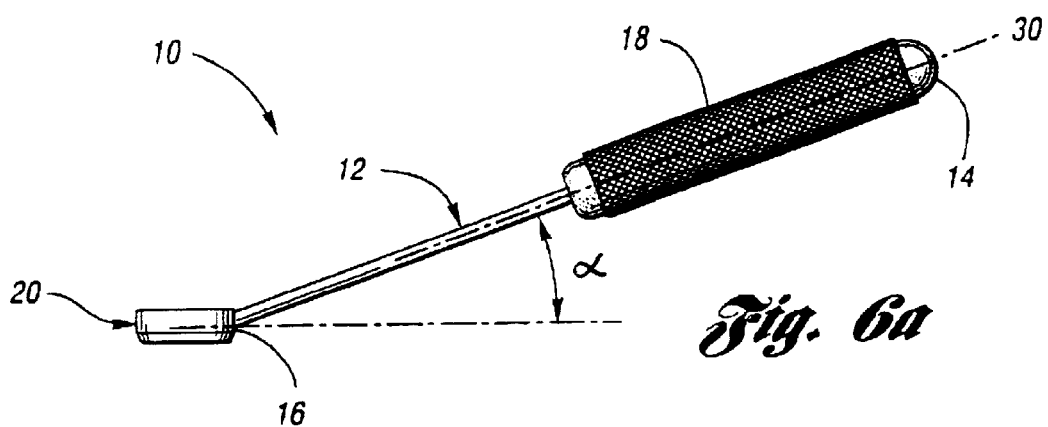
FIG. 6a is a side elevational view of the instrument of FIG. 2a wherein the head portion is attached to the handle at an angle α relative to the longitudinal axis of the handle.
Figure 6B:
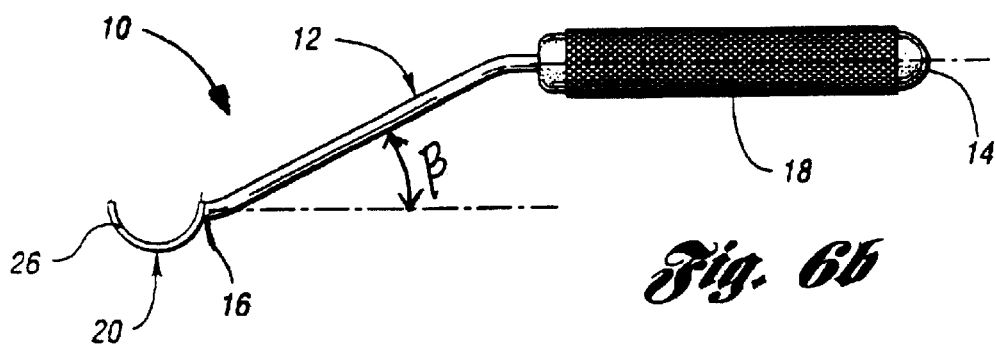
FIG. 6b is a top plan view of the instrument of FIG. 2a wherein the head portion is attached to the handle at an angle β relative to the longitudinal axis of the handle.

FIG. 6a illustrates an embodiment of instrument 10 wherein head portion 20 is attached to handle 12 at an angle α relative to longitudinal axis 30 of the handle 12. This configuration of instrument 10 may be advantageous when performing cataract surgery from above the forehead of the patient. Alternatively, FIG. 6b illustrate head portion attached to handle 12 at an angle β relative to longitudinal axis 30 of the handle 12, which may provide more hand clearance when using additional instruments adjacent instrument 10. Of course, instrument 10 can be configured to include both angles α and β if desired. Handle 12 can also include orientation marks (not shown) to help align the location of head portion 20 and its depth of insertion.

Instrument 10 can either be constructed entirely from a plastic, metallic, or other suitable material, or alternatively from a combination of such materials. More particularly, head portion 20 can be constructed from a medical grade of plastic or surgical steel, both of which can be sharpened to create cutting edge 24. As described below, the sharpness of cutting edge 24 need not be overly precise, since the operator can adjust the pressure applied to the intraocular tissue in order to achieve the particular tissue penetration desired. Advantageously, due to its open curvilinear (e.g. semicircular) design, instrument 10 need not be constructed from flexible materials, as was required in certain prior art devices, in order to accommodate insertion through a small corneal/scleral wound. In fact, given its low cost and ease of manufacture, instrument 10 of the present invention is preferably disposable after use, providing obvious medical benefits with respect to contamination or the like. Alternatively, instrument 10 can be reused as long as its materials of construction are suitable for sterilization. As still another option, handle 12 could be designed to be reusable, and head portion 20 attached to handle 12 in such a way as to be removable and replaceable, similar to a conventional scalpel.

As described above, before an incision can be made on the anterior lens capsule, a small entry wound must be cut on the corneal or scleral tissue of the eye, typically using a keratome, in order to gain access to the anterior chamber. It is desirable to have a small corneal/scleral wound for purposes of promoting wound stability, preventing aqueous leakage, and obviating the need for wound suture. Therefore, the wound length should be less than 4 mm, and most preferably on the order of about 2.5 to 3 to mm in length. However, the diameter of the anterior capsule incision usually must be about 4.5 to 5 mm for proper removal of the natural lens and implantation of an artificial intraocular lens. Due to the open curvilinear, preferably semicircular, design of head portion 20, instrument 10 of the present invention is able to accommodate both of these requirements. In fact, instrument 10 could accommodate even smaller entry wounds, since head portion 20 may be eased through the wound using a curved motion, such that the widest corneal/scleral wound needed would be only slightly larger than the width of head portion 20 itself.

Referring now to FIGS. 7–11, the capsulotomy procedure for the eye 32 is initiated by the-creation of an entry wound 34 in the corneal or scleral tissue 36 in the manner described above. In addition, a paracentesis (not shown) may be created in order to insert additional instruments into the anterior chamber 38, to create a postoperative entrance, or to inject viscoelastic material into the anterior chamber 38. Injecting the anterior chamber 38 with viscoelastic fluid fully expands the chamber 38 prior to use of instrument 10, and can be performed to avoid any tissue damage as head portion 20 is inserted into position for cutting.

Figure 7:
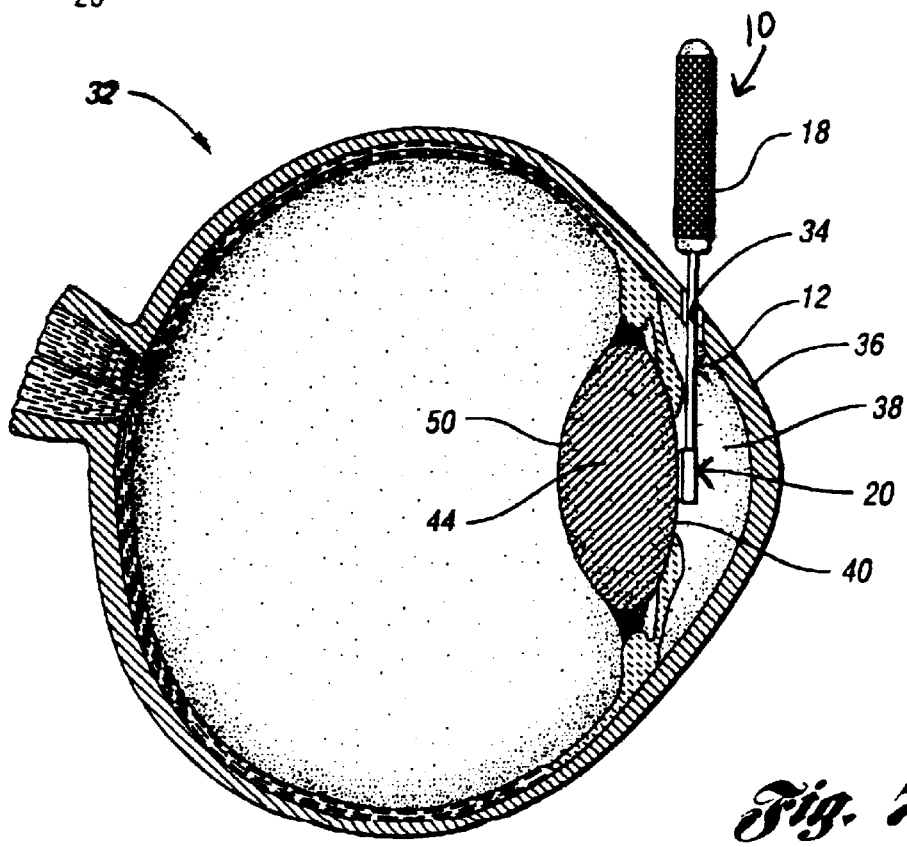
FIG. 7 is a cross-sectional view of the eye illustrating the position of the instrument relative to the eye once the instrument is inserted through the wound cut in the corneal or scleral tissue and brought into proximity with the anterior lens capsule.
Figure 8:
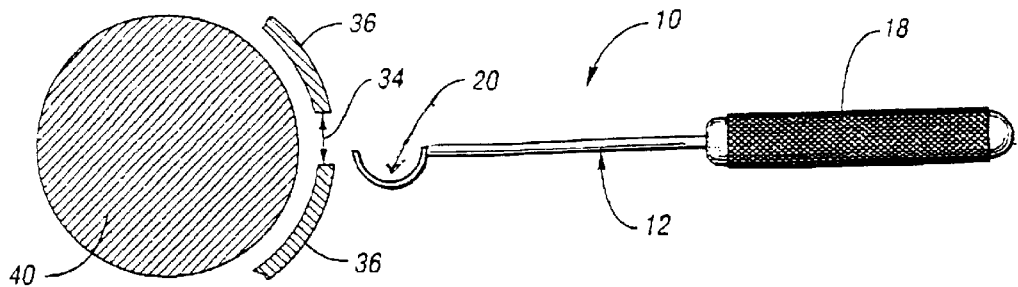
FIG. 8 is a top plan view illustrating the anterior capsule prior to entry of a right-facing instrument in accordance with the present invention through the wound.
Figure 9:
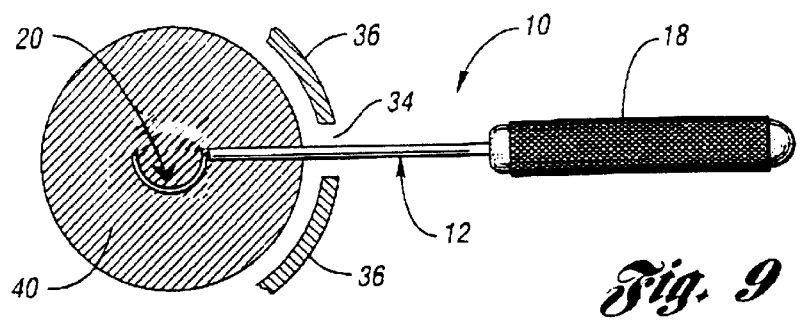
FIG. 9 is a top plan view illustrating the creation of a first generally semicircular incision in the anterior capsule using the instrument of FIG. 8.

As depicted in FIGS. 7–9, head portion 20 of instrument 10 is inserted through the corneal/scleral wound 34, with cutting edge 24 facing down towards the surface of the anterior capsule 40. This process is viewed and monitored by the operator through a microscope, wherein manipulation of instrument 10 requires only one hand. Next, the anterior capsule 40 is engaged with the cutting edge 24 at a desired location, and sufficient pressure is applied to penetrate at least partially through the anterior capsule 40 in order to create a first generally semicircular incision therein 42. The process of engaging and penetrating the anterior capsule 40 may include a slight rotary motion, such that the semicircular incision extends beyond 180°. In fact, cutting edge 24 can be used to completely penetrate the anterior capsule 40 and even cut the lens 44 with no adverse consequences since the lens 44 will be removed during a subsequent procedure. If desired, a non-toxic dye may be applied to cutting edge 24, such that as cutting edge 24 engages the anterior capsule 40, the dye is deposited and leaves a visual imprint along the boundary of the incision 42.

After the first incision 42 is made, instrument 10 is removed through the wound 34, and instrument 10' is inserted therethrough and brought into proximity with the anterior capsule 40. As shown in FIG. 10, the orientation of head portion 20' opposes the orientation of head portion 20 used to make the first incision 42. The anterior capsule 40 is then engaged with cutting edge 24' with sufficient pressure to penetrate at least partially through the anterior capsule 40 in order to create a second generally semicircular incision 46 therein adjacent the first incision 42. The first and second incisions 42, 46 combine to produce a continuous, generally circular tissue flap 48 incised in the anterior capsule 40 (FIG. 11). The tissue flap 48 is subsequently grasped with forceps or the like and pulled along the incisions 42, 46 in order to completely detach the flap 48 from the anterior capsule 40. Although it is described that incision 42 with a right-facing orientation is performed prior to incision 46 having a left-facing orientation, it is understood that the incisions can be performed in any order to create the continuous tissue flap 48.

Alternatively, instrument 110, wherein head portion 120 has two opposed cutting edges 124, 128, can be used to generate the circular tissue flap 48. The anterior capsule 40 is first engaged with cutting edge 124, which penetrates at least partially through the anterior capsule 40 in order to create a first generally semicircular incision therein 42. Next, instrument 110 is rotated approximately 180° about its longitudinal handle axis 130, after which the anterior capsule 40 is engaged with cutting edge 128 in order to penetrate at least partially through the anterior capsule 40, thereby creating a second generally semicircular incision 46 therein adjacent the first incision 42. As with the combination of instruments 10 and 10', use of instrument 110 in this manner results in a generally circular tissue flap 48 incised in the anterior capsule 40.

With the circular flap 48 removed from the anterior capsule 40, phacoemulsification and aspiration procedures or the like can be used to remove the cataractous lens 44, leaving the posterior lens capsule 50 intact to receive the artificial intraocular lens. Ultrasonic energy is used to break up and emulsify the lens nucleus and cortex, a process during which there is a great deal of tension on the cut edges of the anterior capsule 40. The incision created using instrument 10 of the present invention is able to withstand this tension, and prevent tears of the anterior capsule 40 toward the posterior side 50. Once the lens material 44 is completely removed, the artificial intraocular lens (not shown) can be inserted using forceps or other insertion device.

Therefore, instrument 10 of the present invention provides a smooth semicircular cut on one side of the anterior capsule, and then on the other, to form a continuous, complete circular tissue flap without tears or tags. Furthermore, instrument 10 allows for a controlled capsulotomy while requiring only a small corneal or scleral wound. The location of the capsular opening is controlled by the surgeon, and the size of the opening is determined by the dimensions of head portion 20. Instrument 10 is easy to operate and offers a simple and efficient surgery with repeatable results, thereby decreasing cost as well as possibility of intraoperative or postoperative complications. Furthermore, the design of instrument 10 of the present invention makes it simple and cost-effective to manufacture.

Although instrument 10 and the method for its use have been described herein in the context of incising the anterior capsule during a capsulotomy procedure, it should be understood that instrument 10 can be utilized for any surgical procedure where incision of an ocular tissue, or perhaps even other types of tissue, is necessary. For example, an incision similar to that described herein may be required in the posterior capsule during pediatric cataract surgeries. In addition, it is fully contemplated that head portion 20 of instrument 10 can have any curvilinear shape capable of creating an incision suitable for the intended purpose, while still being capable of satisfying the applicable size constraints. Furthermore, it is understood that the numerical values described herein are provided for illustrative purposes only and are typical only for normal situations in cataract surgery. Under other circumstances, different numerical values may apply, and instrument 10 of the present invention can be adapted accordingly.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An instrument for incising an intraocular tissue, comprising:
    a handle; and
    a curvilinear head portion attached to the handle, the head portion having a radius of about 0.5 mm to 4.0 mm and having spaced first and second ends which define an opening therebetween, the head portion including first and second opposed cutting edges wherein the head portion defines a plane and the first and second opposed cutting edges extend from the head portion in directions substantially transverse to the plane,
    wherein the first cutting edge and the second cutting edge are each operable to engage the intraocular tissue and penetrate at least partially therethrough to create curvilinear incisions in the intraocular tissue.

2. The instrument according to claim 1, wherein the head portion is generally semicircular.

3. The instrument according to claim 1, wherein the head portion has a radius of about 2 to 3 mm.

4. The instrument according to claim 1, wherein the head portion has a width of about 1 mm.

5. The instrument according to claim 1, wherein the head portion is attached to the handle at an angle relative to a longitudinal axis of the handle.

6. The instrument according to claim 1, wherein at least one of the handle and the head portion are constructed from a plastic material.

7. The instrument according to claim 1, wherein at least one of the handle and the head portion are constructed from a metallic material.

8. A method for incising an intraocular tissue, comprising:
    creating a wound in one of a corneal region and a scleral region of an eye;
    inserting an instrument through the wound and into proximity with the intraocular tissue, the instrument including a handle and a curvilinear head portion attached to the handle, the head portion having spaced first and second ends which define an opening therebetween, the head portion including cutting edge; and
    engaging the intraocular tissue with the cutting edge and penetrating at least partially through the intraocular tissue without substantial movement of the cutting edge relative to the intraocular tissue in order to create a curvilinear incision therein.

9. The method according to claim 8, wherein engaging the intraocular tissue includes engaging the anterior capsule.

10. The method according to claim 8, wherein creating a wound includes creating a wound less than about 4 mm in length.

11. A method for incising an anterior capsule of an eye, comprising:
    creating a wound in one of a corneal region and a scleral region of the eye;
    inserting a first instrument through the wound and into proximity with the anterior capsule, the first instrument including a handle and a generally semicircular head portion attached to the handle, the first instrument head portion including a cutting edge having a first orientation;
    engaging the anterior capsule with the cutting edge of the first instrument head portion and penetrating at least partially through the anterior capsule in order to create a first generally semicircular incision therein;
    inserting a second instrument through the wound and into proximity with the anterior capsule, the second instrument including a handle and a generally semicircular head portion attached to the handle, the second instrument head portion including a cutting edge having a second orientation which opposes the first orientation; and
    engaging the anterior capsule with the cutting edge of the second instrument head portion and penetrating at least partially through the anterior capsule in order to create a second generally semicircular incision therein adjacent the first incision, thereby resulting in a generally circular tissue flap incised in the anterior capsule.

12. The method according to claim 11, wherein creating a wound includes creating a wound less than about 4 mm in length.

13. The method according to claim 11, further comprising removing the first instrument through the wound prior to inserting the second instrument.

14. The method according to claim 11, further comprising injecting a viscoelastic fluid into an anterior chamber of the eye.

15. The method according to claim 11, further comprising monitoring the first and second instruments with a microscope.

16. The method according to claim 11, further comprising applying a dye to the cutting edge of the first instrument, the dye being deposited on the anterior capsule in response to engagement of the first instrument cutting edge with the anterior capsule.

17. A method for incising an anterior capsule of an eye, comprising:

creating a wound in one of a corneal region and a scleral region of the eye;

inserting an instrument through the wound and into proximity with the anterior capsule, the instrument including a handle and a generally semicircular head portion attached to the handle, the head portion having first and second opposed cutting edges;

engaging the anterior capsule with the first cutting edge and penetrating at least partially through the anterior capsule in order to create a first generally semicircular incision therein;

rotating the instrument approximately 180° about a longitudinal axis of the handle;

engaging the anterior capsule with the second cutting edge and penetrating at least partially through the anterior capsule in order to create a second generally semicircular incision therein adjacent the first incision, thereby resulting in a generally circular tissue flap incised in the anterior capsule.

18. The method according to claim 17, wherein creating a wound includes creating a wound less than about 4 mm in length.

19. The method according to claim 17, further comprising injecting a viscoelastic fluid into an anterior chamber of the eye.

20. The method according to claim 17, further comprising monitoring the instrument with a microscope.

21. The method according to claim 17, further comprising applying a dye to the first cutting edge, the dye being deposited on the anterior capsule in response to engagement of the first cutting edge with the anterior capsule.

22. An instrument for incising an anterior capsule of an eye, comprising:

a handle having a proximal end and a distal end; and a generally semicircular head portion attached to the distal end of the handle, the head portion having a radius of about 0.5 mm to 4.0 mm, the head portion including first and second opposed cutting edges wherein the head portion defines a plane and the first and second opposed cutting edges extend from the head portion in directions substantially transverse to the plane, wherein the first cutting edge and the second cutting edge are each operable to engage the anterior capsule and penetrate at least partially therethrough to create generally semicircular incisions in the anterior capsule.

* * * * *